(12) United States Patent
Scott

(10) Patent No.: US 7,587,290 B2
(45) Date of Patent: Sep. 8, 2009

(54) HIGH WATER CUT WELL MEASUREMENTS USING HEURISTIC SALINITY DETERMINATION

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 0 days.

(21) Appl. No.: 11/762,126

(22) Filed: Jun. 13, 2007

(65) Prior Publication Data

US 2008/0015792 A1    Jan. 17, 2008

Related U.S. Application Data

(60) Provisional application No. 60/813,782, filed on Jun. 15, 2006.

(51) Int. Cl.
  *G01F 1/12* (2006.01)
  *G01F 1/50* (2006.01)
  *G01F 25/00* (2006.01)
  *G01F 1/00* (2006.01)
  *G01F 7/00* (2006.01)
  *G01F 23/00* (2006.01)
  *G01N 11/00* (2006.01)

(52) U.S. Cl. .................. 702/100; 702/45; 702/50; 702/55; 73/61.41; 73/61.43

(58) Field of Classification Search ............. 702/100, 702/45, 50, 55; 73/61.41, 61.43
See application file for complete search history.

(56) References Cited

U.S. PATENT DOCUMENTS

| | | | | | |
|---|---|---|---|---|---|
| 4,352,288 | A | * | 10/1982 | Paap et al. | 73/61.41 |
| 4,852,395 | A | * | 8/1989 | Kolpak | 73/61.44 |
| 4,902,961 | A | * | 2/1990 | De et al. | 324/640 |
| 5,453,693 | A | * | 9/1995 | Sinclair et al. | 324/324 |
| 5,625,293 | A | * | 4/1997 | Marrelli et al. | 324/638 |
| 6,032,539 | A | * | 3/2000 | Liu et al. | 73/861.04 |
| 7,380,438 | B2 | * | 6/2008 | Gysling et al. | 73/19.1 |
| 2007/0224692 | A1 | * | 9/2007 | Agar et al. | 436/150 |

OTHER PUBLICATIONS

Notification Concerning Transmittal of International Preliminary Report on Patentability dated Dec. 31, 2008 in connection with PCT Application No. PCT/US2007/013920.

\* cited by examiner

*Primary Examiner*—Eliseo Ramos Feliciano
*Assistant Examiner*—Janet L Suglo

(57) ABSTRACT

Methods and systems for determining the amount of water in a high water cut crude petroleum flow stream exiting from a hydrocarbon well. Electrical property measurements such as permittivity measurements are collected with a microwave analyzer system as high water cut oil exits from a well. Collection is continued until the span of the measurements of at least one property reaches at least a characteristic pre-determined value. A heuristic salinity of the water phase of the crude oil can then be determined based on the span statistics and reference equations and/or reference data. The flow-weighted average water content of the oil can then be determined using the heuristic salinity to correct for salinity variation as the output of the well changes over time.

17 Claims, 13 Drawing Sheets

| | Salinity, by weight% | | | | | | |
|---|---|---|---|---|---|---|---|
| | 0.10% | 0.50% | 1% | 2% | 3% | 5% | 8% |
| Maximum Frequency, MHz | 222.4 | 213.19 | 210.19 | 205.3 | 201.42 | 195.5 | 189.6 |
| Minimum Frequency, MHz | 214.9 | 205.22 | 199.64 | 191.9 | 187.2 | 180.05 | 171.86 |
| MHz Span Between Max and Min | 7.53 | 7.98 | 10.55 | 13.44 | 14.22 | 15.45 | 17.74 |
| Mean Frequency | 218.7 | 209.21 | 204.91 | 198.6 | 194.31 | 187.77 | 180.73 |
| Slope of Lines on Figure 4, WC %/MHz | -0.066 | -0.063 | -0.047 | -0.037 | -0.035 | -0.032 | -0.0282 |

*FIG. 5*

HIGH WATER CUT WELL MEASUREMENTS USING HEURISTIC SALINITY DETERMINATION

CROSS-REFERENCE TO RELATED APPLICATIONS

This application claims priority from U.S. Provisional Patent Application 60/813,782, filed on Jun. 15, 2006.

BACKGROUND AND SUMMARY OF THE INVENTION

The present application relates to systems and methods for measuring the amount of one phase in a mixture of phases, and more particularly to measuring the amount of water present in crude petroleum oil when the salinity of the water can vary.

The following paragraphs contain some discussion, which is illuminated by the innovations disclosed in this application, and any discussion of actual or proposed or possible approaches in these paragraphs does not imply that those approaches are prior art.

The chemical and physical characterization of crude, partially refined, and fully refined petroleum products is a common practice in the petroleum industry. Characterizations such as compositional and physical property determinations are used for a variety of purposes. One of their more important uses is when they are done in combination with hydrocarbon well testing to assist in optimizing oil production from a single or series of hydrocarbon wells. Another important use is during the transfer of crude petroleum oil, as occurs during the production, transport, refining, and sale of oil. The accurate determination of water content and validation of the amount of water in crude oil is particularly important during the taxation of crude oil and the sale of crude oil, where the owner or seller of the oil does not want to pay taxes on water and the customer does not want to pay the price of oil for water. For example, it is well know to a person having ordinary skill in the art of petroleum engineering that crude petroleum oil emerging from production wells can contain large amounts of water, ranging from generally about 1% to as high as about 99% water. This value is known as the water cut ("WC").

During operation of a high water cut oil well, the oil and water mixture can ideally be considered as a dispersion of oil in water wherein the water is the continuous phase and the oil exists as droplets within the continuous water phase. At water cuts above about 80%, the water is usually the continuous phase and so droplets of the oil are dispersed within the water phase. Additionally, a high water cut oil well typically produces oil with a daily average water cut that can shift over several days or weeks of operation. This is especially true as the oil-bearing formation becomes depleted of oil, resulting in higher and higher amounts of water exiting from the well. However, an oil well is not an ideal system and its compositional behavior can be quite dynamic and random over a period of time as short as several seconds or minutes. For example, water flooding (e.g. water injection from above the ground down into the subterranean oil-bearing formations) can be used to push and carry oil up to the surface of the Earth. At any given moment, more or less water can enter the oil well drill string. This can cause variation in the amount of water in the flow stream exiting from the well. Additionally, as the oil and water mixture travels up the drill string (which can be as long as a mile or more), oil droplets can coalesce into larger collections, or "slugs", of oil. A slug of oil can be considered to be a high concentration of oil with a reduced level of entrained water. Such coalescence of oil then can cause variation in the amount of water exiting a well at any given moment. During operation of a well experiencing oil coalescence, slugs of oil with reduced amounts of water and slugs of water with reduced amounts of dispersed oil can exit from the well. Thus, a water content determination system in contact with the discharge of such a well will be measuring the water content of such slugs.

Water content determinations and validations can be conducted on-line and off-line during petroleum processing. On-line determinations include instruments such as densitometers, capacitance probes, radio frequency probes, and electromagnetic characterization systems, including those which are referred to, for historical reasons, as "microwave analyzers".

U.S. Pat. No. 4,862,060 to Scott (the '060 patent), entitled Microwave Apparatus for Measuring Fluid Mixtures and which is hereby incorporated by reference, discloses electromagnetic characterization systems and methods which are most suitable for monitoring water percentages when the water is dispersed in a continuous oil phase. U.S. Pat. No. 4,996,490 to Scott (the '490 patent), entitled Microwave Apparatus and Method for Measuring Fluid Mixtures and which is hereby incorporated by reference, discloses electromagnetic characterization apparatuses and methods for monitoring water percentages when either oil or water is the continuous oil phase. For the example of oil and water mixtures, the '490 patent discloses that whether a particular mixture exists as an oil-in-water or a water-in-oil dispersion can be determined by differences in the reflected microwave power curves in the two different states of the same mixture. Therefore, the '490 patent discloses magnetic characterization apparatuses and methods, including the ability to measure microwave radiation power loss and reflection to detect the state of the dispersion. In further embodiments of that invention, methods are disclosed to compare the measured reflections and losses to reference reflections and losses to determine the state of the mixture as either water-in-oil or oil-in-water, which then allows the proper selection and comparison of reference values relating the measured microwave oscillator frequency to the percentage water. An embodiment of the '490 patent is reproduced from that patent in FIG. 1A.

Salinity in the water associated with crude oil presents a further challenge to such water cut determination systems and methods because salinity has a significant effect on the electromagnetic properties of the oil and water mixture. Additionally, the amount of salinity in the water can vary, even from the same well. For example, water percolation within subterranean oil-bearing formations can change course over time resulting in changing amounts of dissolved salts in the water. One method of correcting for the effects of salinity changes is for an operator to manually measure the salinity of the water phase and input the measurement into the analyzer to allow it to select pre-established offset correction factors, based on the inputted salinity and test-generated calibration curves. A manual determination of salinity is commonly made using a refractometer to measure the refractive index of the water phase. This index is then correlated to % salinity using a pre-established relationship between % salinity and refractive index. The % salinity is then entered into the analyzer as previously described. The pre-established relationship between % salinity and refractive index can be developed by measuring the refractive index of a series of standardized saline solutions to establish a data reference set and equations can be fitted to the data set.

Sometimes, the refractive index of the aqueous phase cannot be easily determined. For example, the aqueous phase may be so turbid as to prevent an accurate reading from being obtained. Or, in the case of an emulsified oil-water system, the refractive index cannot be read unless the system is somehow de-emulsified and allowed to separate into a clear-enough aqueous phase to allow a refractive index to be determined.

Such refractive index measurement techniques or other separate salinity measurement techniques are thus inherently unreliable in systems that are susceptible to emulsification and require additional apparatus, further complicating the total measurement system.

Other laboratory methods will analyze the produced water for ionic content and a "total dissolved solids" and the "equivalent NaCl" contents can be determined. Since different salts, e.g. NaCl, KCl, etc. all have different conductivities (and these change with electromagnetic frequency), it is difficult to know what number is appropriate to use. Many times the "total dissolved salts" will be used as equivalent NaCl. These numbers are inexact and will lead to real time errors of measurement. In addition, the samples are always at room temperature and do not reflect the conductivity of the ion at the operating temperature of the production fluids. Additionally, such off-line methods do not offer the advantage of automatic and continuous monitoring.

One approach to accommodate the effects of variable salinity is to use a joint densitometry and electromagnetic characterization system and method. See U.S. patent application Ser. No. 11/490,541, entitled "Autocalibrated Multiphase Fluid Characterization Using Extrema of Time Series," by Bentley N. Scott, filed Jul. 20, 2006, Patent Publication Document Number US 2007-0038399 A1. The '541 application is a dual instrument approach. An approach using only a single instrumental method such as a single electromagnetic characterization system (e.g. a single microwave analyzer) is also desirable.

High Water Cut Well Measurements Using Heuristic Salinity Determination

Systems and methods to determine the water cut of a high water cut oil flowing from a hydrocarbon production well. Live electromagnetic characterization data is collected from the oil-water mixture discharging from a well until the characteristic span of an electrical property measurement is achieved. Hindsight processing of at least one of the span's statistics is used to determine the aqueous phase salinity of the oil using salinity reference values. The determined salinity can then be used to calculate the water cut of the oil.

In some embodiments (but not necessarily all), the disclosed ideas are used to estimate the water phase fraction and the oil phase fraction in a crude petroleum oil flow stream exiting from an oil production well with a range of water cuts from substantially 1% to substantially 100%.

The disclosed innovations, in various embodiments, provide one or more of at least the following advantages:

Some of the disclosed innovations provide methods and systems to reduce measurement uncertainties caused by variable salinity in an aqueous phase of a multiphase fluid flow stream.

Some of the disclosed innovations provide more accurate physical or electrical property measurements in an oil and water mixture flow stream.

Some of the disclosed innovations provide near-real-time reduction of errors and supply more accurate results to aid in near-real-time decision-making, without requiring multiphase fluid flow stream sampling or off-line labwork conducted on such samples and thus eliminating the cost, lost opportunities, and hazards associated with such sampling.

BRIEF DESCRIPTION OF THE DRAWINGS

The disclosed innovations will be described with reference to the accompanying drawings, which show important sample embodiments of the invention and which are incorporated in the specification hereof by reference.

FIG. 5 is a table of data illustrating key aspects of the graph in FIG. 4 according to the present innovations.

DETAILED DESCRIPTION OF THE PREFERRED EMBODIMENTS

The numerous innovative teachings of the present application will be described with particular reference to the presently preferred embodiment (by way of example, and not of limitation).

Figure 2:
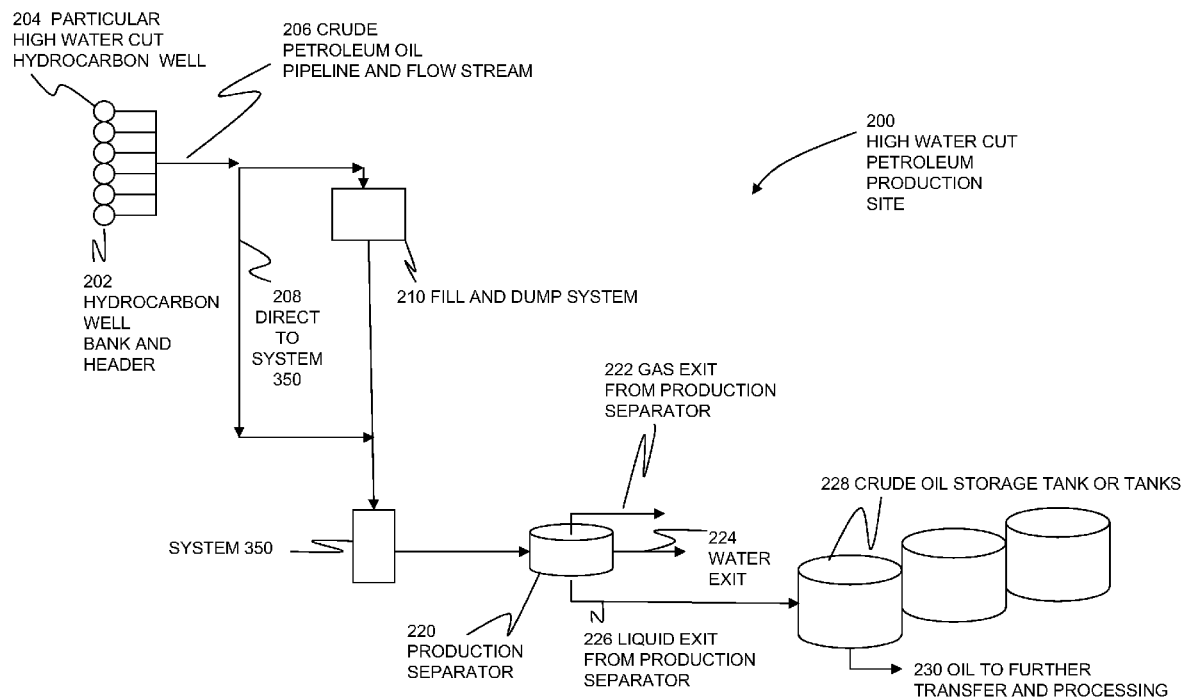
FIG. 2 is a diagram of an exemplary hydrocarbon production site at which the methods and systems of the present innovations can be implemented.

FIG. 2 shows a high water cut hydrocarbon production site 200 according to an illustrative, non-limiting embodiment consistent with the present application at which the methods and systems of the present innovations can be implemented. A pipeline 206 carrying a high water cut petroleum flow stream can lead from a set of petroleum-producing wells 202 or a particular well 204 of which all or some may be located on land or under-sea. The high water cut well measurement system 350 (e.g. which can be an electromagnetic characterization system) can receive the flow from the pipeline either directly via pipe 208 or via a fill and dump metering system 210 as known to one skilled in oil field operations. This location can be close to the wellhead, for example, or further down the pipeline leading from the wellhead. In the case of off-shore hydrocarbon wells, it can alternatively be performed on an offshore platform or a floating production ship. System 350 can be positioned between wells 202 and a production gas-liquid separator 220, which is upstream of a storage tanks 228. Stream 224 represents the separated water phase leaving separator 220 whereas stream 222 is the separated gas leaving the separator.

Figure 1:
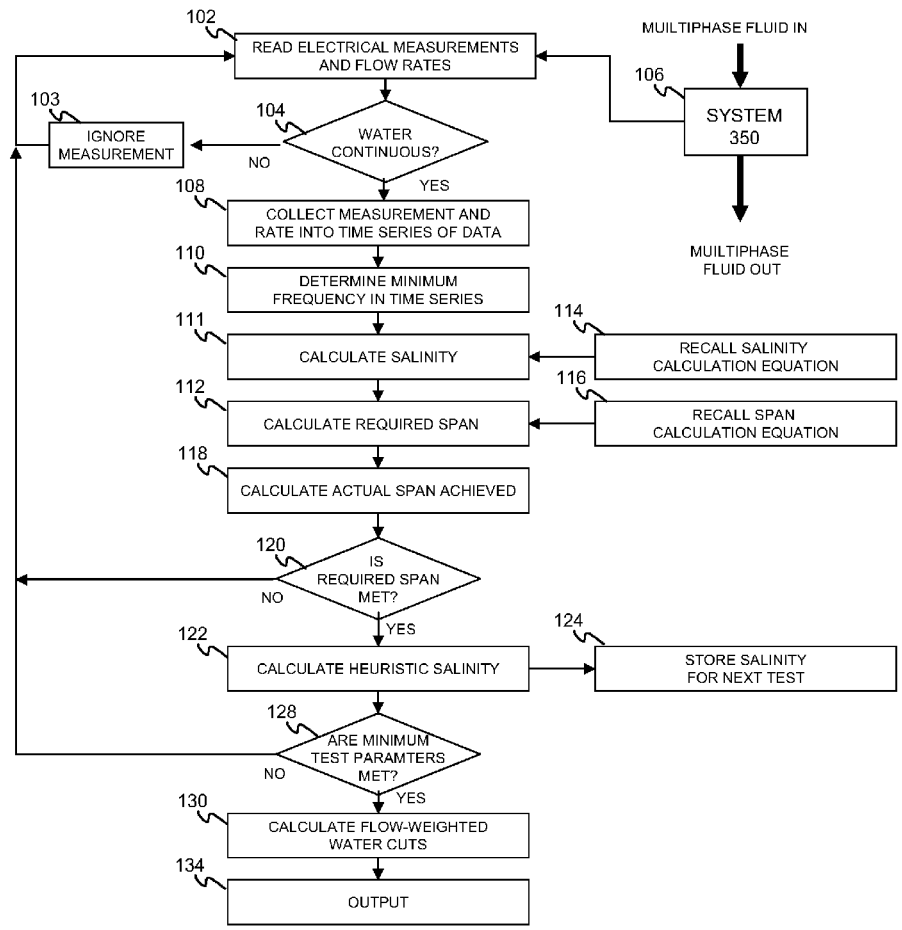
FIG. 1 is a preferred embodiment of a method for water cut determinations according to the present innovations.
Figure 1A:
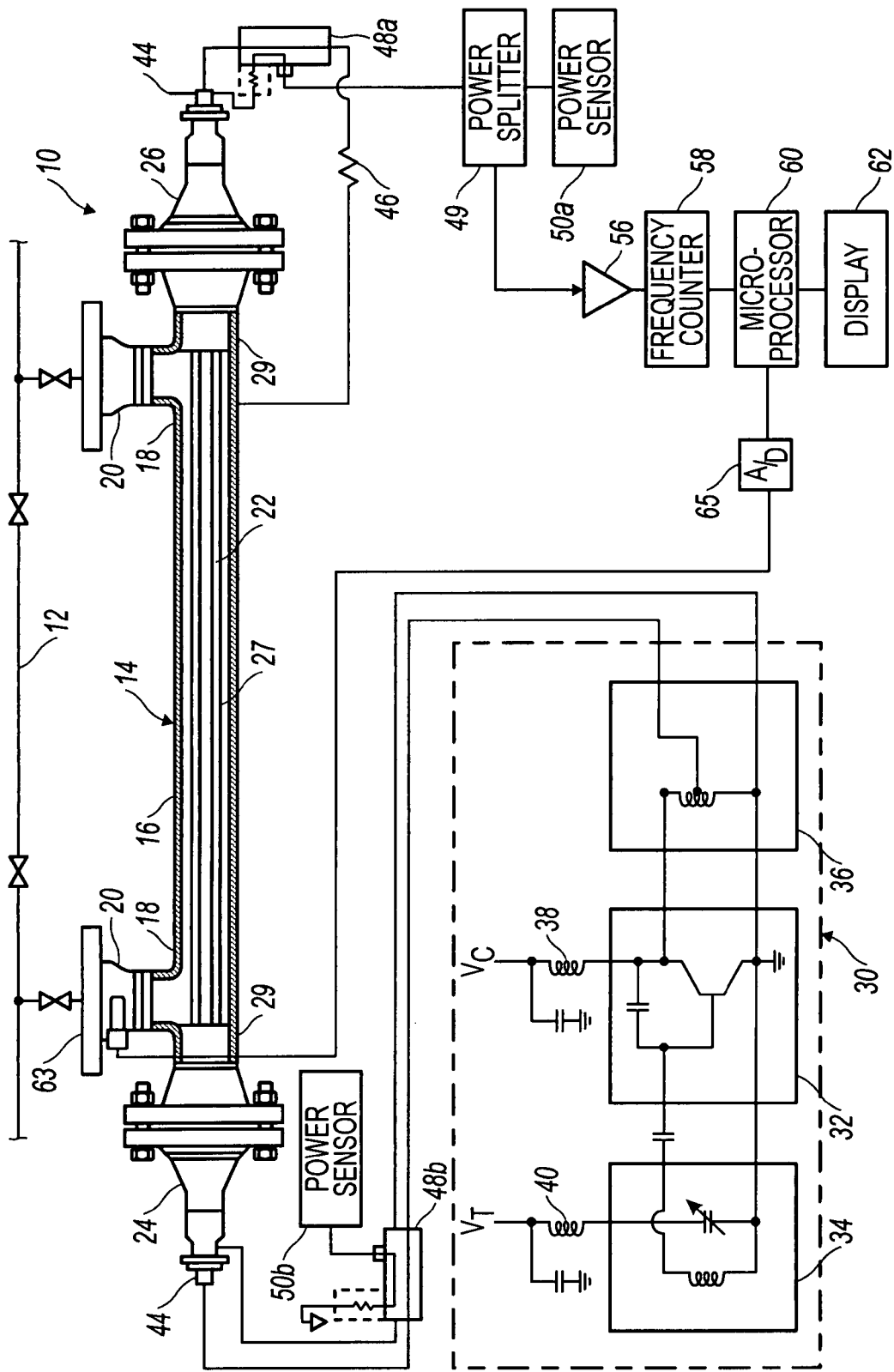
FIG. 1A is a preferred embodiment of an electromagnetic characterization apparatus for use with the methods and systems of the present innovations.
Figure 3:
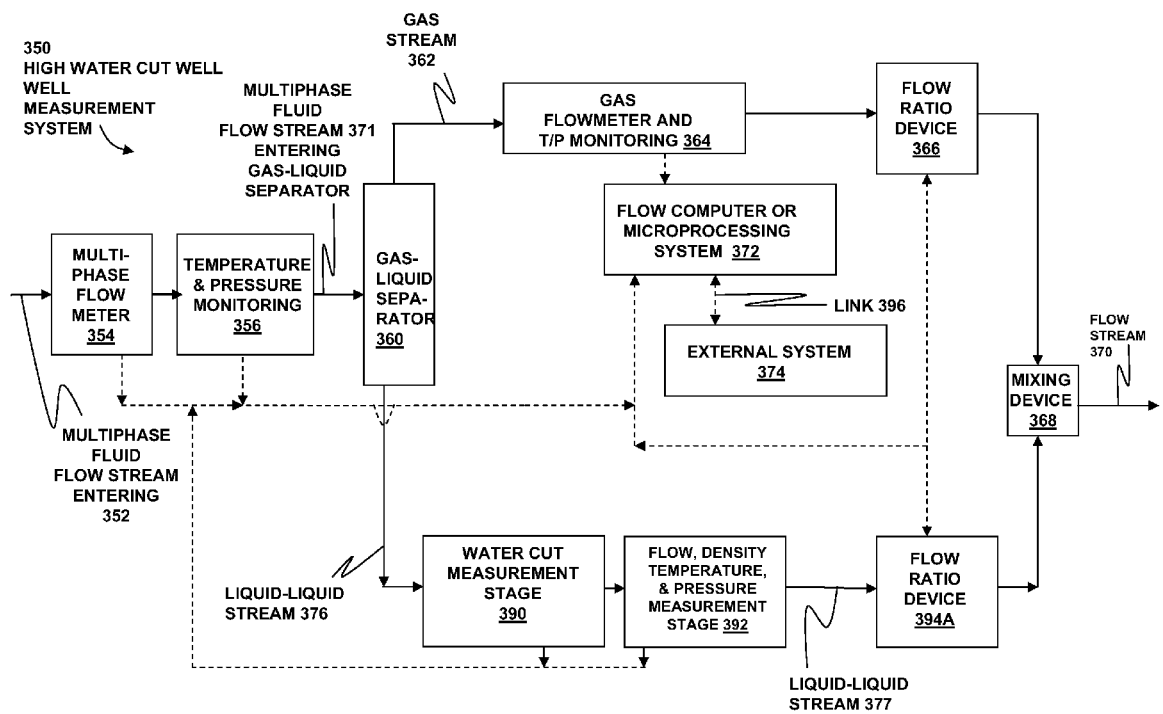
FIG. 3 is a preferred embodiment of a high water cut well measurement system of the present innovations.

Turning now to FIG. 1A, water-cut electromagnetic characterization analyzers can perform the function of water-cut measurement in stage 390 of FIG. 3. U.S. Pat. No. 4,996,490 describes some of the preferred embodiments of water-cut electromagnetic characterization analyzers to be used in the present application. FIG. 1A is a reproduction of FIG. 1 from U.S. Pat. No. 4,996,490 as an example of one embodiment of the present innovations of an electromagnetic characterization analyzer that can be used with the present innovations. Specifically, FIG. 1A shows illustrated a diagram of an apparatus for measuring the concentration of one substance or material such as water, in another substance or material such as crude petroleum oil, which is being transmitted as a liquid mixture flow stream through a pipeline. The apparatus is generally designated by the numeral 10 and is particularly adapted for interconnection with a fluid transmission pipeline 12 for sampling the pipeline flow stream. Alternatively, the apparatus 10 might become part of the pipeline. The apparatus 10 includes a fluid flow conducting and measurement section 14 comprising an outer conduit section 16, including spaced apart pipe tee sections 18 having conventional flange portions 20 formed thereon for connection to branch conduit portions of the pipeline 12. The measurement 14 comprises a coaxial transmission line which includes a center conductor 22 preferably formed of a metal such as stainless steel which extends between opposed end support parts 24 and 26 which are described in detail in the above-referenced patent application. The center conductor 22 preferably comprises a generally cylindrical rod or tube member coaxially arranged in the conduit 16 and provided with an outer sheath 27 formed of a material having a relatively low dielectric loss tangent, preferably less than 0.1 at a frequency of 1.0 GHz. The sheath 27 preferably comprises a relatively easy-to-fabricate plastic such as polypropylene, a plastic sold under the trademark Delrin or one of the fluorocarbon plastics. Alternatively, certain ceramics or other materials may also be used as the outer sheath 27 as long as they are low loss tangent dielectric materials. The fit between the outer sheath 27 and the center conductor 22 is preferably a forced or line-to-line fit although some clearance may be permitted as long as fluid flow between the center conductor and the outer sheath is prohibited. In an apparatus where the center conductor has a diameter of 0.25 inches, the outer diameter of the sheath 27 is preferably at least about 0.50 inches or, alternatively, a ratio of the outer diameter of the sheath to the outer diameter of the center conductor is in the range of about two to one.

It has been determined that with the provision of a sheath 27 formed of one of the above-mentioned materials and in the proportions described, that the electrical circuit for propagating microwave radiation through the apparatus 22 retains a high quality signal resolution characteristic in liquid mixtures of oil and water, for example, wherein the water content is relatively high, that is on the order of more than 5% to 10% by volume. With this type of center conductor arrangement, the circuit associated with the apparatus 10 and described herein below retains good field intensity or prevents short circuiting of the center conductor to the outer conductor in an unwanted location, the oscillator circuit retains its good load-pulling characteristics with good resolution of phase and the interface between the sheath 27 and the fluid in the conduit 16 is a new propagation medium which has desirable operating characteristics.

When the apparatus 10 is operating with a liquid composition which is high in water content or a so-called water continuous phase, the conductivity of the composition is high compared to a good dielectric but low compared to a good conductor and, of course, the liquid composition is in direct contact with the wall surfaces of the measurement section 14 including the center conductor. The insulating sheath 27 prevents the radio frequency (RF) energy (e.g. microwave energy) from being shorted out immediately at the point where the RF energy enters the measurement section or where the fluid cross section begins. Moreover, the sheath 27 now becomes the primary region where the RF field is propagated with the conductive fluid becoming a pseudo outer wall of the measurement section in place of the wall of the conduit 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section. The dielectric structure is now the sheath 27. The properties of the propagated RF energy still reflect the changing content of the oil in the water and this is related through pulling of the unisolated oscillator which is described herein below. The sheath 27 must be thick enough to maintain a reasonable coaxial impedance to be able to propagate the RF energy into the measurement section 14 and maintain a measurement capability. A very thin dielectric coating on the center conductor 22 will cause very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or, low conductivity, this depth into the conductor increases rapidly. This phenomenon is known in the art as skin depth.

As shown in FIG. 1A, the center conductor 22 extends through opposed end block members 29 which are also preferably formed of a relatively high insulative material such as a fluorocarbon plastic and the end plug sections are configured in a way similar to the ones described in the above-referenced patent application.

The measurement section 14 is operably connected to a source of radio frequency (RF) or so-called microwave energy comprising an unbuffered or unisolated, free-running oscillator, generally designated by the numeral 30. The oscillator 30 includes an active circuit 32 operably connected to a tuning circuit 34 and to an impedance matching network circuit 36. The circuit 32 is adapted to receive a constant DC voltage, $V_c$, from a source not shown and by way of a filter circuit 38. The tuning circuit 34 is also adapted to receive a controllable DC voltage, $V_t$, from another source, not shown, by way of a second filter circuit 40. The oscillator 30 has an appreciable load-pulling characteristic. The fundamental operating frequency of the oscillator is changed as the complex load is changed on the output circuit of the oscillator. The oscillator 30 is preferably of a type commercially available such as from Avantek Company, Santa Clara, Calif. as their model VTO 8030 voltage controlled oscillator. The exemplary oscillator 30 has a maximum load-pulling characteristic of about 35 MHz at a nominal 200 MHz operating frequency into all phases of a short circuit at the end of a 50 Ohm line stretcher (approximately 0.5 DB return loss). The oscillator 30 is operably connected to the apparatus measurement section 14 through a suitable connector 44 which is in electrically conductive engagement with the center conductor 22 at the end part 24 and at the opposite end of the center conductor 22 through a second connector 44, a resistance 46 and with the outer conductor or conduit 16 as illustrated. The end part 26 is also adapted to connect the center conductor 22 with a 10 DB directional coupler 48a which is operable to sample the microwave energy or power transmitted through the coaxial measurement section 14. The coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50 may be of a type 437B manufactured by Hewlett Packard of Sunnyvale, Calif.

A second directional coupler 48b is interposed in the circuit between the end part 24 and the oscillator 30 and is connected to a second power sensor 50b. The directional couplers 48a and 48b may be of identical configuration. The coupler 48a is connected to the power splitter 49 which provides an output signal which is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A and the microprocessor 60 may be a Hewlett Packard type 9836. The system illustrated in FIG. 5 preferably includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator. For example, the oscillator 30, in a preferred form, can be pulled from its nominal operating frequency through a range of about 20 MHz by the changing dielectric constant of the medium flowing through the measurement section 14.

Turning now to FIG. 3, a high water cut measurement system 350 (e.g. an electromagnetic characterization system) is depicted according to an illustrative, non-limiting example of a preferred embodiment consistent with the present application, for measuring the water cut of a multiphase fluid, such as the gases and liquid petroleum recovered from a hydrocarbon well or wells. The petroleum can be a liquid stream comprising an oil phase and a water phase, with entrained non-condensed gas. A gas-liquid-liquid multiphase fluid flow stream 352 can enter the system. The flow rate of flow stream 352 can be monitored at 354. Temperature and pressure of the flow stream can be monitored at 356. Multiphase flow stream 371 can enter gas-liquid separator 360 wherein a condensible and/or non-condensible gas fraction can be separated from the multiphase fluid to a degree consistent with the composition and physical properties of the multiphase fluid and its components, as well as the design and operating parameters of gas-liquid separator 360 as known to a person having ordinary skill in the design and operations of gas-liquid separators. The gas fraction flow stream 362 exits separator 360 and the flow rate, temperature, and pressure can be monitored at 364. The flow ratio of gas flow stream 362 to a liquid flow stream separated by separator 360 can be maintained by a suitable device at 366. Gas-liquid production separators are described in Chapter 12 of the third printing of the Petroleum Engineering Handbook, Howard B. Bradley editor-in-chief, Society of Petroleum Engineers, 1992, hereby incorporated by reference. FIGS. 12.23 and 12.25 from the Petroleum Engineering Handbook show schematics of typical production gas-liquid separators as can be used as separator 360. A liquid-liquid mixture (e.g. oil dispersed in a continuous water phase) flow stream 376 can be monitored for water-cut at 390 and can be monitored for density, flow rate, temperature, and pressure at 392. Note however that a preferred embodiment of the present innovations does not require density monitoring to perform a water cut analysis. The representative flow rate ratio of stream 376 to stream 362 can be maintained on stream 376 by a suitable device at 394A. Streams 376 and 362 can be combined in mixing or combining device 368 and then exit system 350 as stream 370. Measuring components 354, 356, 390, 392, and 364 can all or selectively be electrically coupled to flow computer or microprocessor system 372 which in one embodiment of the present innovations, can perform and output the calculations of, for example, the method of FIG. 1. In another embodiment, flow computer or microprocessor system 372 can transmit or output collected measurements to external system 374 where the measurements can be stored or other calculations can be performed, including, for example, the method of FIG. 1.

Figure 4:
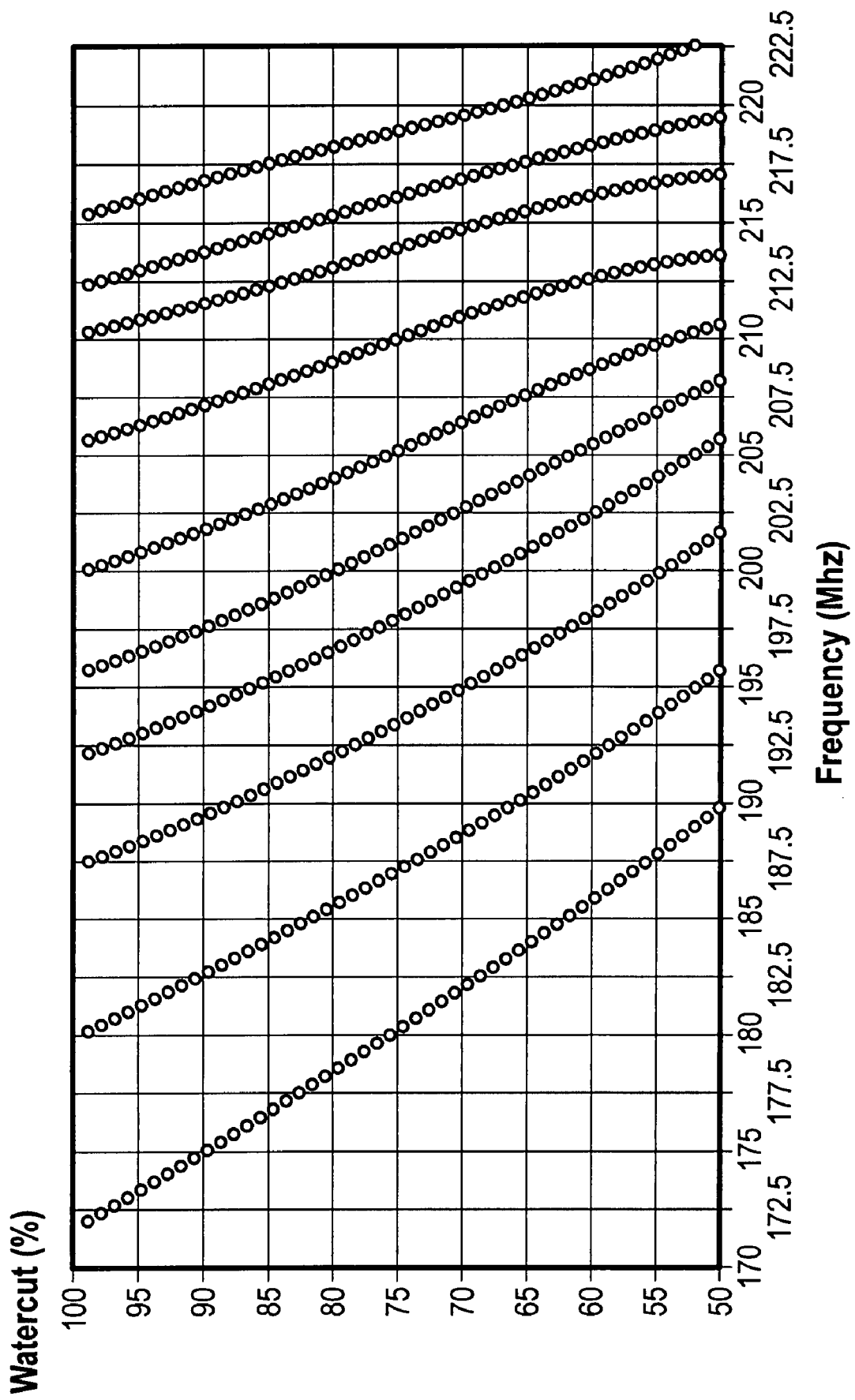
FIG. 4 is a graph of a family of water cut versus permittivity frequency calibration curves for different salinities of a water phase according to the present innovations.

Turning now to FIG. 4, calibration curves were assembled to relate the electromagnetic (e.g. electrical) properties for water-continuous dispersions of oil to the water content of such mixtures. Specifically, curves relating salinity, water cut, and microwave permittivity frequency in MHz (f) were constructed using a high water cut measurement system substantially similar to system 350. For the frequency curves, water cut percentages ranged from 50% to 100% and were tested at salinities including 0.1%, 0.2%, 0.3%, 0.5%, 1.0%, 1.5%, 2.0%, 3.0%, 5.0%, and 8.0%. FIG. 4 shows the resulting family of curves. Note that an equation can be fitted to the family of curves.

Turning now to FIG. 5, the table of data shows the minimum, mean, and maximum frequencies for the family of curves. The spans between the minimum and maximum frequencies, and the slopes of the lines on FIG. 4 are also detailed. Note that the minimum frequency also corresponds to 100% WC, e.g. zero oil content. Thus, the minimum is the permittivity frequency of the pure saline water phase. Note that an equation or equations can be fitted to the data and values in FIG. 5.

Figure 5A:
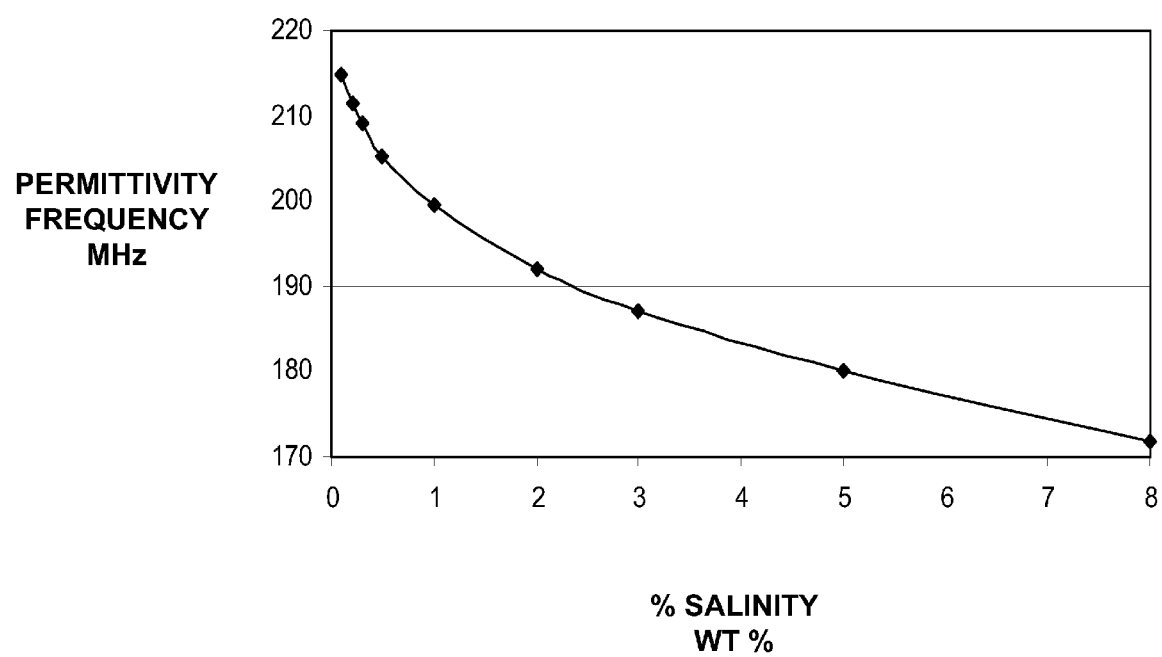
FIG. 5A shows a graph relating permittivity frequency to salinity for the aqueous phase with zero oil content according to the present innovations.

Turning now to FIG. 5A, a graph shows the relationship between permittivity frequency and salinity for the saline water phase at 100% WC, e.g. zero oil content. Note that an equation can be fitted to the data in FIG. 5A.

Figure 5B:
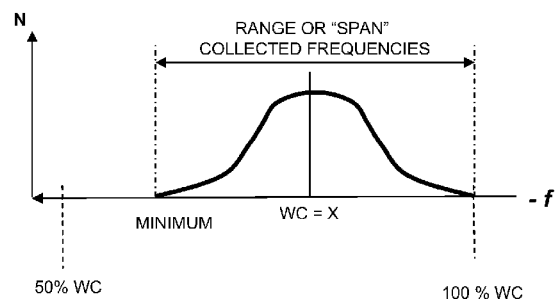
FIGS. 5B, 5C, and 5D show exemplary histograms of electrical property readings and waters of a high water cut crude petroleum oil emerging from an oil production well according to the present innovations.
Figure 5C:
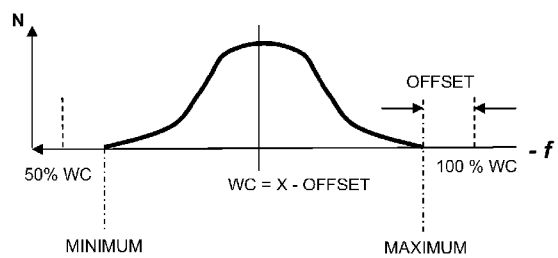
Figure 5D:
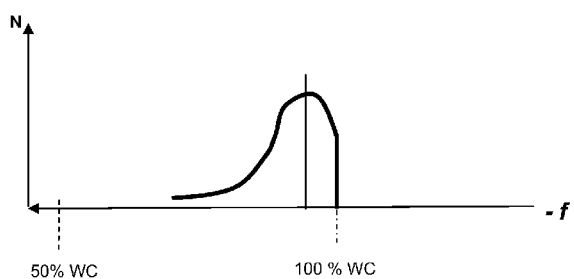

Turning now to FIGS. 5B through 5D, a series of graphs show hypothetical histograms of negatived frequency measurements taken by an electromagnetic characterization system such as system 350 directly in contact with a flow stream from a high water cut oil well prior to any further processing of the flow stream such as the location shown in FIG. 2 where system 350 receives the well or wells output through line 208.

In these histograms, the flow stream is assumed to always be water-continuous and the salinity is assumed to be constant over the length of the collection of the readings. The vertical axis of each histogram depicts the number of readings whereas the horizontal axis depicts the negatived frequency of a particular reading. In this case, since salinity is assumed to be constant, the horizontal axis can also be considered to represent the water content of the flow stream. Thus, the histograms also depict the distribution of the hypothetical water cuts from a high water cut oil well.

FIG. 5B shows a histogram with a normal distribution of negatived frequencies (e.g. water cuts). In this instance, the average water cut is shown as "X" and the minimum and maximum are also shown. Because the water content cannot exceed 100%, the right tail of the distribution stops at 100% water cut. Note that the range or "span" of the water cuts is also shown stretching from the minimum to the maximum of the distribution.

FIG. 5C shows a similar histogram but in this instance, the average water cut is shown as "X minus offset" where the maximum water content encountered in the readings is 100% minus the offset.

FIG. 5D shows a non-normal distribution of readings wherein the average water content is high enough and close enough to 100% such that the right half of the distribution is truncated.

In actual operation of a high water cut oil well, it has been found that most wells produce some output that is substantially 100% water for short periods of time. Such would be the case as shown in FIG. 5B and FIG. 5D. In those instances, the minimum frequency encountered represents the frequency of the aqueous phase. By utilizing the graph of FIG. 5A (or an equation fitted to the graph), the salinity of the well output can thus be determined. Once the salinity is determined, the water cut measurements from an electromagnetic characterization system such as a microwave water cut analyzer can be corrected for the change in the salinity from a previously inputted salinity. A problem with utilizing this approach is knowing when enough readings have been gathered to then select the minimum frequency as the frequency of the aqueous phase. If the distribution is as in FIG. 5D, the truncated shape can indicate that a substantially pure water phase has been read a multiple of times. Thus, one can rely on the minimum frequency as substantially equal to the frequency of the aqueous phase (e.g. 100% WC) if the output of the well is not emulsified. However, if the distribution is normal and the output of the well is non-emulsified, then the "length" of the tails of the distribution will tend to "grow" over time as more readings are collected on the random variations of water content in the flow stream exiting from the well. FIG. 5 shows the span in MHz of frequency, at different salinities, between the minimum and maximum frequency corresponding to water cuts of 100% and 50%, respectively. If the typical salinity and range of water cuts is known for a given well, then a span of typical frequencies can be determined. For example, if a given well swings between 50% and 100% WC at 2% salinity then the characteristic span of frequencies is 13.44 MHz. Thus, a span of 13.44 MHz can be used to test when enough readings have been collected such that the minimum frequency corresponds to the pure aqueous phase at 2% salinity. However, the salinity of the well can change over time, either upwards or downwards. If the salinity shifts downwards to, for example, 1.9%, then the span of 13.44 MHz would never be achieved unless the well swings through a wider range of water contents than 50% to 100%. To that point, a slightly reduced span can be applied to account for the downward shift in salinity. Thus, a heuristic salinity can be derived.

FIG. 1 shows a preferred embodiment of the present innovations as heuristic salinity and water cut method 100. In method 100, system 350 as stage 106 can read and collect electromagnetic characterization (e.g. electrical) measurements on a multiphase fluid flow stream such as crude petroleum oil exiting from a high water cut well as stage 102 of the method. Then, a continuous phase check can be made at stage 104 using the innovations disclosed in the '490 Patent to Scott as previously discussed. If the flow stream at a particular time is oil continuous (such as when a slug of substantially pure oil passes through system 350), then stage 103 can ignore the measurement for the purpose of determining the heuristic salinity. However, the reading will be maintained for the final calculation of average flow weighted water cut in stage 130. If stage 104 finds the flow stream when it is water continuous, then method 100 can collect the measurement and flow rate into a time series of data. Note that data is usually stored as a time series but that the time is not determinative for a heuristic salinity determination. Next, stage 110 can find the minimum frequency in the time series. Next, stage 111 can calculate the salinity of the of the flow stream by recalling the last or historical salinity in stage 114. Stage 114 can then use a salinity calculation equation such as an equation fitted to the data for the graph of FIG. 5A that can estimate the salinity of the flow stream. Stage 112 can then calculate the required span to be achieved in the collection of the frequencies by recalling a span calculation equation in stage 116 such as an equation fitted to the data and values in FIG. 5. The calculation can use either a historical salinity or the salinity determined in stage 110 to calculate the required span. Note that stage 112 can set a required span slightly lower than that determined by stage 116. Stage 118 can calculate the actual span of frequencies achieved by determining the difference between the highest and lowest frequency collected so far. Stage 120 can check to determine if the actual span exceeds the required span. If the actual span is less than the required span, then method 100 loops back to stage 102 to collect more readings. If the actual span meets or exceeds the required span, then a final heuristic salinity can be calculated in stage 122 using an equation fitted to the data used in FIG. 5A. Stage 124 can store the heuristic salinity for the next test to be used in stage 114. Next, method 100 can check whether the water cut determination test parameters have been met in stage 128. For example, a minimum time of collection of water cut and flow rate data can be required to determine the average water cut for the well for fiscal purposes. If not, method 100 loops back to stage 102 to collect more readings. If the minimum criteria has been met, then stage 130 can calculate the flow weighted water cuts using the frequencies gathered in stage 102, the heuristic salinity determined in stage 122 and the graph of FIG. 4, or equations fitted to the graph, an equation relating frequency to water cut for oil-continuous mixtures, and flow rate readings for the flow stream (to enable flow-weighted calculations). Method 100 then outputs the average water cut for the test in stage 134.

Example 1

According to the present innovations, a water cut measurement experiment was run using a high water cut petroleum production site such as site 200 of FIG. 2. The particular well was known to be a high water cut well operating above 80% WC, but the exact WC % was not known. Crude petroleum oil from the well was directed to a fill and dump metering system, such as system 210. In fill and dump systems, a petroleum flow stream generally enters an un-agitated tank within the system. When a tank in the system is near full, a valve opens to quickly drain the tank, and then closes to repeat the cycle.

This fill and dump operation can result in "cyclic gravity settling" wherein the water settles fully or partially to the bottom of the tank. In this experiment, a microwave analyzer system, such as system 350 analyzed the outlet of the cycling fill and dump system and collected a time series of frequency measurements. Note that in another embodiment, system 350 can analyze the output of hydrocarbon wells directly, such as using pipeline and flow stream 208 in FIG. 2.

Figure 6:
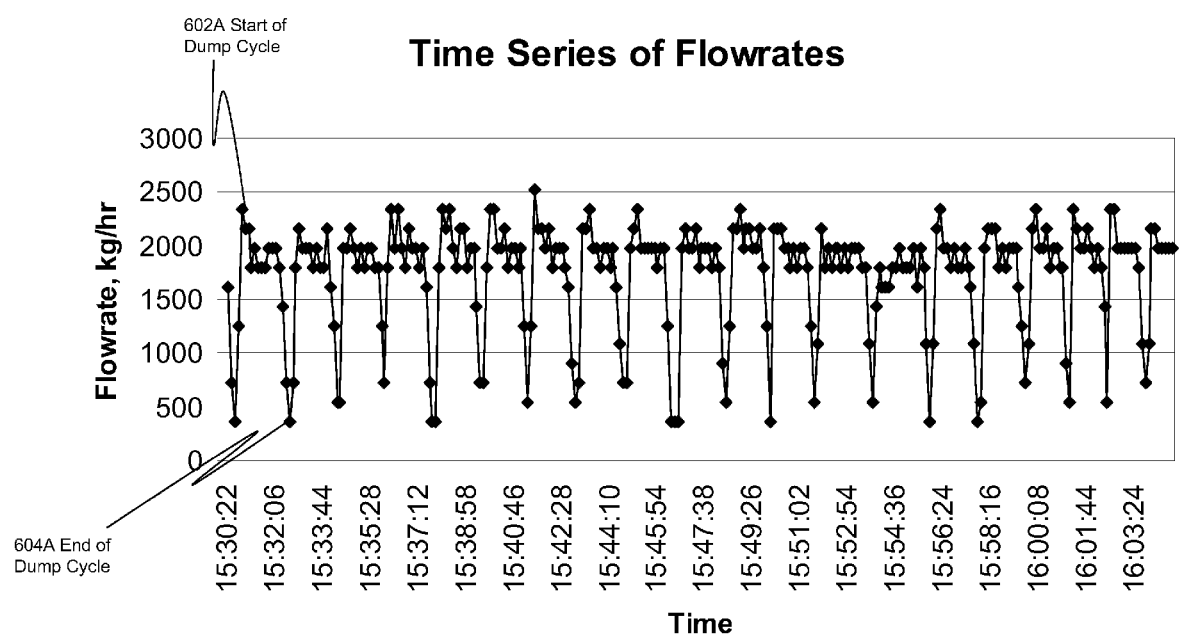
FIG. 6 is a time series graph of flow rate versus time for Example 1 according to the present innovations.

Turning now to FIG. 6, a graph shows the time series of 278 data points of mass flow rates taken over a 35 minute period of operation of a fill and dump system (such as system 210) time using either flow meter 354 or stage 392 to gather the flow rate data. In this example, the amount of gases were negligible so the results of either meter will suffice.

Figure 7:
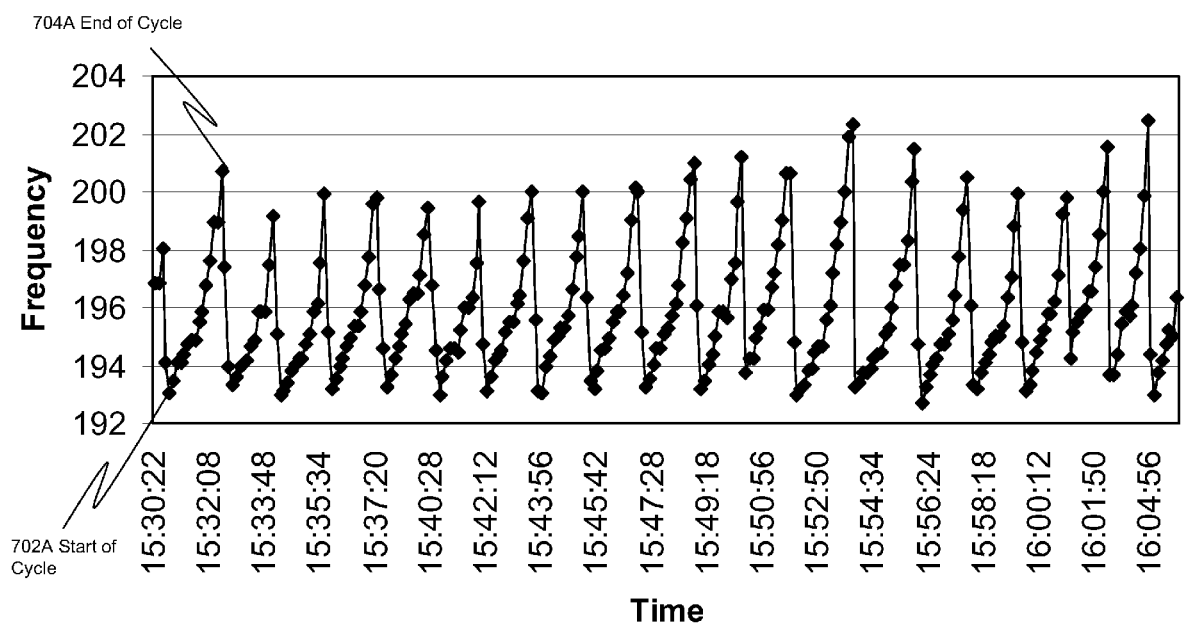
FIG. 7 is a time series graph of permittivity frequency versus time for Example 1 according to the present innovations.

Turning now to FIG. 7, a graph shows the corresponding series (of the same 278 data points taken at essentially the same time) of permittivity frequencies taken on the petroleum flow stream using system 350. In FIGS. 6 and 7, time points 602A and 702A approximately correspond to the start of a dump cycle of system 408, and 604A and 704A approximately correspond to the finish of a dump cycle.

From FIG. 6 and FIG. 7, the batch cycle for the fill and dump was about 40 seconds. In FIG. 6, the flow rate is high at the start of each dump cycle and drops as the tank drains, due to the decrease in head pressure. Additionally, during such a 40 second period, oil will begin to rise to the top of the tank, thus increasing the water cut at the bottom of the tank. Upon dumping, the first fluid to exit is thus a higher water cut, as evidenced by the lower frequency readings at the start of each dump cycle in FIG. 7. An example start of a dump cycle is labeled as 702A on FIG. 1 and the end of a cycle is labeled 704A.

Figure 8:
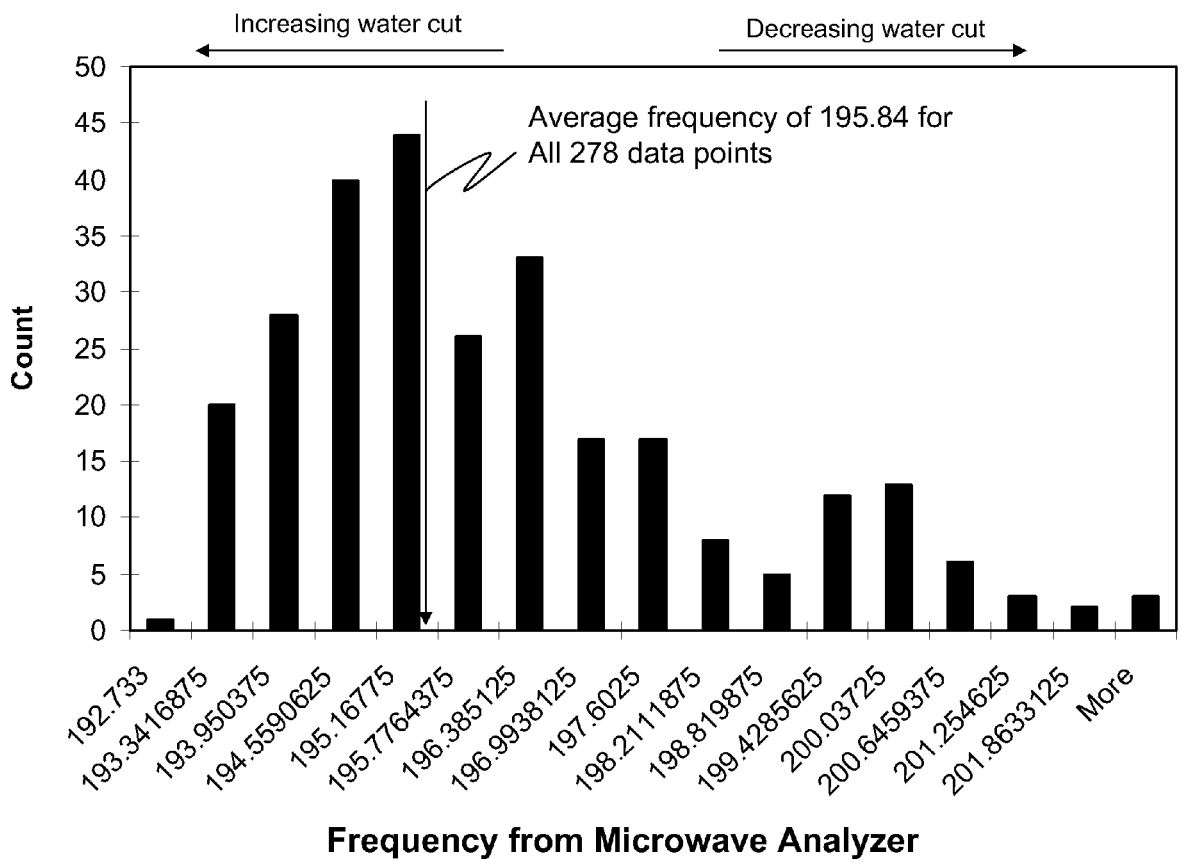
FIG. 8 is a histogram of permittivity frequency readings for Example 1 according to the present innovations.

Turning now to FIG. 8, a graph shows a histogram of the same 278 frequency readings from FIG. 7. From FIG. 8, it is apparent that the process produces a skewed distribution. The average microwave frequency reading of the 278 data points is 195.84. The flow-weighted average of the 278 points is 194.44. The histogram shows a truncated distribution of readings, non-normally distributed from the average frequency. The histogram also shows a virtually absolute minimum frequency of 192.733, which abruptly halts the distribution towards higher water cuts. The explanation for the abrupt absolute minimum frequency of the distribution is that the maximum possible water cut of 100% is represented by the minimum frequency in the data as explained previously for FIG. 5D. Thus, using the graph of FIG. 5A, the heuristic salinity is determined by interpolation to be 1.9%. Using this salinity and the flow-weighted frequency of 194.44 MHz with interpolation of the data and values of FIG. 5, the average WC was found to be 93.5% WC.

According to a disclosed class of innovative embodiments, there is provided a method for heuristically determining the water content of a multiphase fluid flow stream, comprising the actions of: (a) collecting electrical measurements of a multiphase fluid flow stream; wherein said collecting action is continued until the difference between the minimum and maximum of at least one of said measurements equals or exceeds a pre-determined value; (b) calculating the aqueous phase salinity of said stream based on at least said minimum; (c) calculating the water content of said flow stream based at least on (b); whereby salinity-dependent uncertainty is reduced; and (d) outputting the results of (c).

According to a disclosed class of innovative embodiments, there is provided a system for heuristically determining the water content of a multiphase fluid flow stream, comprising the actions of: a multiphase crude oil petroleum fluid flow stream; and a water content measurement system in contact with said flow stream; wherein said measurement system can: (i) collect electrical measurements of said stream; wherein said collecting action is continued until the difference between the minimum and maximum of at least one of said measurements equals or exceeds a pre-determined value; (ii) calculate the aqueous phase salinity of said stream based on at least said minimum; (iii) calculate the water content of said flow stream based at least on (ii); and (iv) output the results of action (iii); whereby said system reduces salinity-dependent uncertainty in water content measurements of crude petroleum flow streams.

According to a disclosed class of innovative embodiments, there is provided a method for heuristically determining the water content of a multiphase fluid flow stream, comprising the actions of: (a) flowing crude petroleum oil directly from a hydrocarbon production well through a pipe to a microwave water cut analyzer system; (b) collecting electrical properties of said flowing oil with said system; (c) calculating the span between the minimum value and maximum value of one of said properties; (d) determining the salinity of the water associated with said oil when said span is at least equal to a previously determined span for said well; and (e) calculating the water content of said oil using at least said salinity.

According to a disclosed class of innovative embodiments, there is provided a method for heuristically determining the water content of a multiphase fluid flow stream, comprising the actions of: (a) determining the range of water content and aqueous salinity of a first quantity of crude petroleum oil produced from an oil well; (b) determining the span of an electrical property across said range; (c) measuring said electrical property of a second quantity of oil flowing from said well until the range of the property measurements is substantially equal to the span determined in (b); (d) determining the salinity of the water associated with said second quantity of oil based at least on the minimum value of said property determined in (c); (e) calculating the water content of said second quantity of oil based at least on said salinity; and (f) outputting the results of (e).

According to a disclosed class of innovative embodiments, there is provided a method for heuristically determining the water content of a multiphase fluid flow stream, comprising the actions of: (a) determining the range of an electrical property of a first quantity of crude petroleum oil produced from an oil well; (b) measuring said electrical property of a second quantity of oil flowing from said well until the range of the property measurements is substantially equal to the range determined in (a); (c) calculating the water content of said second quantity of oil based at least on a salinity value determined at least on the minimum value of the range of (b); and (d) outputting the results of (c).

Modifications and Variations

As will be recognized by those skilled in the art, the innovative concepts described in the present application can be modified and varied over a range of applications, and accordingly the scope of patented subject matter is not limited by any of the specific exemplary teachings given. It is intended to embrace all such alternatives, modifications, and variations that fall within the spirit and broad scope of the appended claims.

The methods and systems of the present application can operate across a wide range of hydrocarbon well service fluid provision situations and conditions. One of ordinary skill in the art, with the benefit of this disclosure, will recognize the appropriate use of the methods and systems for a chosen application of a given or dynamic set of operating parameters.

Optionally, the methods and systems of the present innovations can utilize the slope of the lines of FIG. 4 as another means of heuristically determining the salinity of an aqueous phase.

Figure 10:
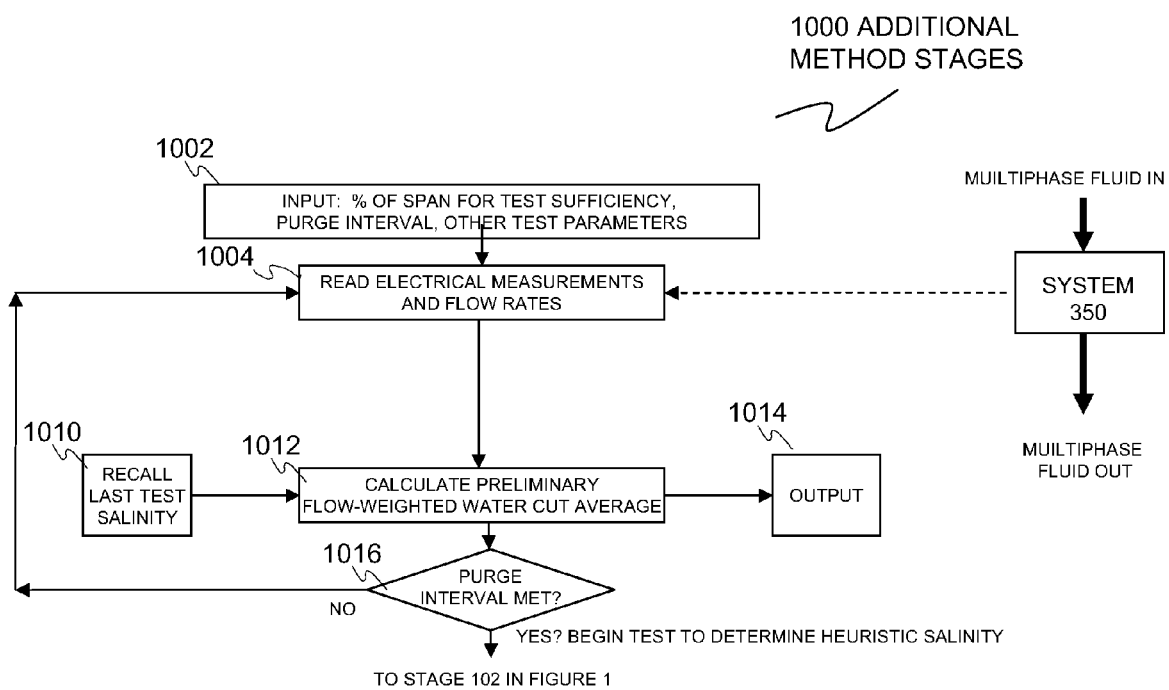
FIG. 10 is one embodiment of additional stages for the method of FIG. 1, according to the present innovations.

Optionally, the method of FIG. 1 can be expanded to include the additional method stages 1000 in FIG. 10. Stage 1002 can receive an input of the percent of span for heuristic test sufficiency. This input can be used to calculate the required span as described for stage 112 in FIG. 1. Stage 1002 can also receive an input of the required purge time interval to, for example, clear a well upon start-up prior to beginning an actual well test. Other test parameters can also be inputted. Stage 1004 can read electrical properties of the multiphase fluid flowing through system 350. Stage 1012 can calculate a preliminary flow weighted water cut and output the results in stage 1014. To calculate the water cuts, stage 1010 can input the last historical salinity into stage 1012. This historical salinity can be retrieved from stage 124 in FIG. 1. Stage 1016 can conduct the purge interval test according to the inputted purge interval.

Optionally, flags such as a particular process variable out of range which may define the reliability of the data or provide variables to use for process control. One of ordinary skill in the art, with the benefit of this disclosure, will recognize the appropriate additional measurements that would be beneficial for a chosen application.

Optionally, such measurements taken by the methods and systems of the present application may also be sent to an external system for further processing or use. For example, if operating conditions exceed a target by a certain amount, this fact could be used to re-tune process controllers. Or, for example, flow rates having a large standard deviation beyond a preset level might be used for the same flagging determination to re-tune flow rate controllers.

Optionally, temperature compensation can be employed used to adjust for shifts in density using reference data sets relating temperature change to total fluid density change, or curves fitted to such reference data.

Optionally, because the density changes of different fluid compositions or recipes can vary from application to application, or across different embodiments, different reference data sets or curves or models fitted to such data sets may be employed, maintained, or stored in flow computer 372 or an external system 374 connected to flow computer 372. One of ordinary skill in the art, with the benefit of this disclosure, will recognize the appropriate systems to employ for such temperature compensation methods.

Figure 9:
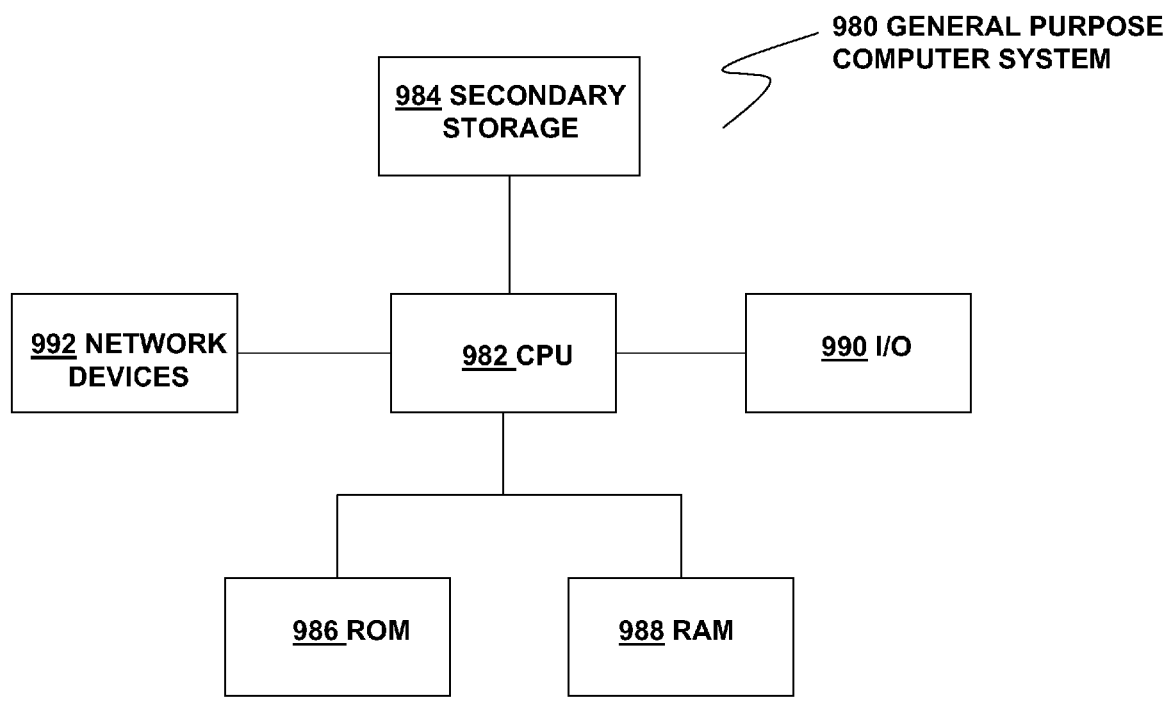
FIG. 9 is general purpose computer system in which the methods of the present innovations can be embodied in, according to the present innovations.

The methods and systems of the present innovations can be implemented on any general-purpose computer with sufficient processing power, memory resources, and network throughput capability to handle the necessary workload placed upon it. FIG. 9 illustrates a typical, general-purpose computer system 980 suitable for implementing one or more embodiments of the several control system embodiments disclosed herein. The computer system 980 includes a processor 982 (which may be referred to as a central processor unit or CPU) in communication with memory devices including secondary storage 984, read only memory (ROM) 986, random access memory (RAM) 988, input/output (I/O) devices 990, and network connectivity devices 992. The processor may be implemented as one or more CPU chips. The secondary storage 984 typically comprises one or more disk drives or tape drives and is used for non-volatile storage of data and as an over-flow data storage device if RAM 988 is not large enough to hold all working data. Secondary storage 984 may be used to store programs that are loaded into RAM 988 when such programs are selected for execution. The ROM 986 is used to store instructions and perhaps data that are read during program execution. ROM 986 is a non-volatile memory device which typically has a small memory capacity relative to the larger memory capacity of secondary storage 984. The RAM 988 is used to store volatile data and perhaps to store instructions. Access to both ROM 986 and RAM 988 is typically faster than to secondary storage 684. I/O devices 990 may include printers, video monitors, liquid crystal displays (LCDs), touch screen displays, keyboards, keypads, switches, dials, mice, track balls, voice recognizers, card readers, paper tape readers, or other well-known input devices. The network connectivity devices 992 may take the form of modems, modem banks, ethernet cards, universal serial bus (USB) interface cards, serial interfaces, token ring cards, fiber distributed data interface (FDDI) cards, wireless local area network (WLAN) cards, radio transceiver cards such as Global System for Mobile Communications (GSM) radio transceiver cards, and other well-known network devices. These network connectivity devices 992 may enable the CPU 982 to communicate with an Internet or one or more intranets. With such a network connection, it is contemplated that the CPU 982 might receive information from the network, or might output information to the network in the course of performing the above-described method steps. Such information, which is often represented as a sequence of instructions to be executed using processor 982, may be received from and outputted to the network, for example, in the form of a computer data signal embodied in a carrier wave. Such information, which may include data or instructions to be executed using processor 982 for example, may be received from and outputted to the network, for example, in the form of a computer data baseband signal or signal embodied in a carrier wave. The baseband signal or signal embodied in the carrier wave generated by the network connectivity devices 992 may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art. The processor 982 executes instructions, codes, computer programs, scripts which it accesses from hard disk, floppy disk, optical disk (these various disk based systems may all be considered secondary storage 984), ROM 986, RAM 988, or the network connectivity devices 992.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle. The claims as filed are intended to be as comprehensive as possible, and NO subject matter is intentionally relinquished, dedicated, or abandoned.

What is claimed is:

1. A method for heuristically determining the water content of a multiphase fluid flow stream, comprising the actions of:
  (a) collecting a series of electrical measurements of a single multiphase fluid flow stream using a microwave water cut analyzer until a difference between a minimum and a maximum of said measurements equals or exceeds a pre-determined value;
  (b) calculating an aqueous phase salinity of said single stream based on at least said minimum;
  (c) calculating a water content of said single flow stream based at least on (b); and
  (d) outputting the results of (c);
  wherein said calculated salinity is updated in real time if:
    (i) additional measurements are collected; and
    (ii) a lower minimum of said measurements is determined in said additional measurements.

2. The method of claim 1, wherein said measurements are at least partly determined from calculations.

3. The method of claim 1, wherein gases in said single stream are substantially removed prior to collecting said measurements.

4. The method of claim 1, wherein said measurements correspond to a permittivity of said single stream.

5. The method of claim 1, wherein the water content calculated in action (c) is a flow-weighted water content.

6. The method of claim 1, wherein the single multiphase fluid flow stream is a crude petroleum oil flow stream exiting from a hydrocarbon production well.

7. A system for heuristically determining the water content of a multiphase fluid flow stream, comprising:
- a single multiphase crude oil petroleum fluid flow stream; and
- a water content measurement system in contact with said flow stream; wherein said measurement system is configured to:
  (i) collect a series of electrical measurements of said single stream until a difference between a minimum and a maximum of said measurements equals or exceeds a pre-determined value;
  (ii) calculate an aqueous phase salinity of said single flow stream based on at least said minimum;
  (iii) calculate a water content of said single flow stream based at least on (ii); and
  (iv) output the results of action (iii);
- whereby said system reduces salinity-dependent uncertainty in water content measurements of crude petroleum flow streams;
- wherein said calculated salinity is updated in real time if:
  (i) additional measurements are collected; and
  (ii) a lower minimum of electrical measurements is determined in said additional measurements.

8. The system of claim 7, wherein said measurements are at least partly determined from calculations.

9. The system of claim 7, wherein gases in said single flow stream are substantially removed prior to collecting said measurements.

10. The system of claim 7, wherein said measurements correspond to a permittivity of said single flow stream.

11. The system of claim 7, wherein the water content calculated in action (iii) is a flow-weighted water content.

12. The system of claim 7, wherein said measurements are collected using a microwave water cut analyzer.

13. The system of claim 7, wherein said measurements are collected on a single crude petroleum oil flow stream:
  (i) directly exiting from a hydrocarbon production well; and
  (ii) before said single stream is further processed or stored at a hydrocarbon production site.

14. The system of claim 7, wherein said measurements are collected on a single crude petroleum oil flow stream:
  (i) exiting from a hydrocarbon production well; and
  (ii) after said single stream is subjected to a cyclic gravity-settling process at a hydrocarbon production site.

15. A method for heuristically determining the water content of a multiphase fluid flow stream, comprising the actions of:
  (a) flowing crude petroleum oil directly from a hydrocarbon production well through a pipe to a microwave water cut analyzer system;
  (b) collecting a series of measurements of an electrical property of said flowing oil with said system;
  (c) calculating a span between a minimum value and a maximum value of said property;
  (d) determining a salinity of the water associated with said oil when said span is at least equal to a previously determined span for said well;
  (e) calculating a water content of said oil using at least said salinity; and
  (f) outputting the results of (e);
- wherein said determined salinity is updated in real time if:
  (i) additional measurements are collected; and
  (ii) a lower minimum value of said measurements is determined in said additional measurements.

16. A method for heuristically determining the water content of a multiphase fluid flow stream, comprising the actions of:
  (a) determining a range of a water content and an aqueous salinity of a first quantity of crude petroleum oil produced from an oil well;
  (b) determining a span of an electrical property across said range;
  (c) measuring said electrical property of a second quantity of oil flowing from said well for a series of measurements using a microwave water cut analyzer until a range of the property measurements of the second quantity of oil is substantially equal to the span determined in (b), the range having a minimum value and a maximum value;
  (d) determining a salinity of the water associated with said second quantity of oil based at least on the minimum value of said property determined in (c);
  (e) calculating a water content of said second quantity of oil based at least on said salinity; and
  (f) outputting the results of (e);
- wherein said determined salinity is updated in real time if:
  (i) additional measurements are collected; and
  (ii) a lower minimum value of said measurements is determined in said additional measurements.

17. A method for heuristically determining the water content of a multiphase fluid flow stream, comprising the actions of:
  (a) determining a range of an electrical property of a first quantity of crude petroleum oil produced from an oil well over a first series of measurements, the range having a minimum and a maximum value;
  (b) measuring said electrical property of a second quantity of oil flowing from said well over a second series of measurements using a microwave water cut analyzer until a range of the property measurements of the second quantity of oil is substantially equal to the range determined in (a), the range having a minimum and a maximum value;
  (c) calculating a water content of said second quantity of oil based at least on a salinity value determined at least on a minimum value of the range of (b); and
  (d) outputting the results of (c);
- wherein said determined salinity is updated in real time if:
  (i) additional measurements are collected; and
  (ii) a lower minimum value of said measurements is determined in said additional measurements.

* * * * *